US012620481B2

(12) United States Patent
Frenzel et al.

(10) Patent No.: US 12,620,481 B2
(45) Date of Patent: May 5, 2026

(54) AUTOMATIC REGISTRATION OF AT LEAST ONE DEVICE IN A LABORATORY SYSTEM

(71) Applicant: Roche Diagnostics Operations, Inc., Indianapolis, IN (US)

(72) Inventors: Matthias Frenzel, Mannheim (DE); Javier Martinez Fernandez, Mannheim (DE); Ramona Seel, Mannheim (DE)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 131 days.

(21) Appl. No.: 18/562,880

(22) PCT Filed: May 20, 2022

(86) PCT No.: PCT/EP2022/063713
§ 371 (c)(1),
(2) Date: Nov. 21, 2023

(87) PCT Pub. No.: WO2022/243511
PCT Pub. Date: Nov. 24, 2022

(65) Prior Publication Data
US 2024/0242826 A1       Jul. 18, 2024

(30) Foreign Application Priority Data
May 21, 2021     (EP) ..................................... 21175338

(51) Int. Cl.
*G16H 40/40*           (2018.01)
(52) U.S. Cl.
CPC .................................... *G16H 40/40* (2018.01)
(58) Field of Classification Search
CPC ...................................................... G16H 40/40
(Continued)

(56) References Cited

U.S. PATENT DOCUMENTS

| | | | | |
|---|---|---|---|---|
| 7,535,854 | B2 * | 5/2009 | Luo ...................... | H04L 61/5014 |
| | | | | 370/254 |
| 7,680,605 | B2 * | 3/2010 | Yung ...................... | G16H 40/63 |
| | | | | 340/3.1 |

(Continued)

FOREIGN PATENT DOCUMENTS

| | | |
|---|---|---|
| EP | 1 926 429 B1 | 8/2015 |
| EP | 3 056 320 A1 | 8/2016 |

(Continued)

OTHER PUBLICATIONS

International Preliminary Report on Patentability for related PCT/ EP2022/063713 mailed May 3, 2023.
(Continued)

*Primary Examiner* — Michael Tomaszewski
(74) *Attorney, Agent, or Firm* — Woodard, Emhardt, Henry, Reeves & Wagner, LLP

(57) ABSTRACT

A computer-implemented method of automatic registration of a device in a laboratory system comprising:
    transmitting from the to be registered device specific information to a managing unit ("unit") via a first interface;
    the unit requesting a solution specific configuration from a remote infrastructure via a second interface, receiving the solution specific configuration from the remote infrastructure via the second interface, and transmitting the solution specific configuration to the device to be registered via the first interface, the solution specific configuration being based on the device specific information and configuration information about the laboratory system; and
    transmitting a request from the unit comprising updated solution specific configuration to the laboratory devices, the updated solution specific configuration comprising information about the device to be regis- (Continued)

Figure 1:
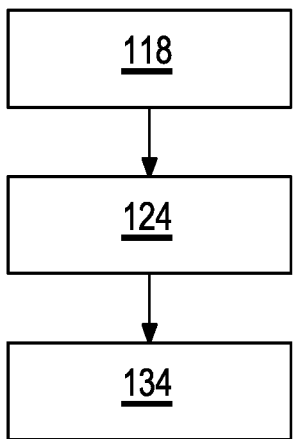

tered and changes due to addition of said device, wherein the laboratory configuration step comprising providing the updated solution specific configuration to the remote infrastructure.

16 Claims, 1 Drawing Sheet

(58) Field of Classification Search
USPC ........................................................ 705/2–3
See application file for complete search history.

(56) References Cited

U.S. PATENT DOCUMENTS

| | | | | |
|---|---|---|---|---|
| 7,694,809 | B2 * | 4/2010 | Garbini | A61M 25/0133 |
| | | | | 206/364 |
| 8,225,015 | B2 * | 7/2012 | Gao-Saari | G06F 13/102 |
| | | | | 710/64 |
| 8,549,065 | B2 * | 10/2013 | Mahnke | G06F 9/543 |
| | | | | 709/203 |
| 8,806,473 | B2 * | 8/2014 | Birtwhistle | G06F 8/65 |
| | | | | 713/168 |
| 10,797,947 | B2 * | 10/2020 | Heimes | H04W 12/35 |
| 11,262,370 | B2 * | 3/2022 | Oosterbroek | G01N 35/00871 |
| 2004/0121299 | A1 * | 6/2004 | Rougeau | G09B 5/06 |
| | | | | 434/365 |
| 2005/0038676 | A1 * | 2/2005 | Showalter | G06Q 10/06 |
| | | | | 705/2 |
| 2005/0106736 | A1 * | 5/2005 | Yung | G05B 23/0264 |
| | | | | 422/68.1 |
| 2005/0149283 | A1 * | 7/2005 | Herrmann | A61B 90/90 |
| | | | | 702/85 |
| 2006/0026205 | A1 * | 2/2006 | Butterfield | G16H 20/10 |
| 2006/0133362 | A1 * | 6/2006 | Stein | G06F 9/441 |
| | | | | 370/360 |
| 2007/0282175 | A1 * | 12/2007 | Urbaszek | G16H 40/40 |
| | | | | 600/300 |
| 2008/0059239 | A1 * | 3/2008 | Gerst | H04W 12/06 |
| | | | | 707/E17.107 |
| 2010/0287006 | A1 * | 11/2010 | Cannon | G06Q 10/06 |
| | | | | 455/414.1 |
| 2010/0318699 | A1 * | 12/2010 | Gao-Saari | G16H 40/40 |
| | | | | 710/72 |

| | | | | |
|---|---|---|---|---|
| 2011/0001605 | A1 * | 1/2011 | Kiani | G16H 50/50 |
| | | | | 235/492 |
| 2012/0110200 | A1 * | 5/2012 | Ahn | G06Q 10/06 |
| | | | | 709/230 |
| 2012/0226768 | A1 * | 9/2012 | Gaines | G16H 40/67 |
| | | | | 709/217 |
| 2012/0324063 | A1 | 12/2012 | Huan et al. | |
| 2014/0152466 | A1 * | 6/2014 | Wiesner | A61B 5/0026 |
| | | | | 340/870.07 |
| 2015/0151131 | A1 * | 6/2015 | Huelskamp | A61N 1/025 |
| | | | | 607/59 |
| 2019/0072575 | A1 * | 3/2019 | Oosterbroek | G01N 35/0092 |
| 2020/0116745 | A1 * | 4/2020 | Frenzel | G01N 35/02 |
| 2020/0275273 | A1 | 8/2020 | Smith et al. | |
| 2020/0382599 | A1 * | 12/2020 | Knafel | H04L 67/5651 |
| 2020/0400697 | A1 * | 12/2020 | Sinz | G01N 35/00613 |
| 2020/0411176 | A1 * | 12/2020 | Hadorn | G05B 23/0283 |
| 2022/0137079 | A1 * | 5/2022 | Oosterbroek | G16H 10/40 |
| | | | | 422/500 |
| 2024/0242826 | A1 * | 7/2024 | Frenzel | G16H 40/40 |

FOREIGN PATENT DOCUMENTS

| | | | | |
|---|---|---|---|---|
| EP | 3 412 603 A1 | 12/2018 | | |
| EP | 3 451 253 | 3/2019 | | |
| EP | 3451253 A1 * | 3/2019 | ......... | G06Q 10/0631 |
| JP | 2002117196 | 4/2002 | | |
| JP | 2002117196 A * | 4/2002 | | |
| JP | 2006084308 | 3/2006 | | |
| JP | 2012105713 | 6/2012 | | |
| WO | WO-2005031631 A2 * | 4/2005 | ............ | G16H 40/20 |
| WO | WO 2015/011274 A2 | 1/2015 | | |
| WO | WO-2022243511 A1 * | 11/2022 | ............ | G16H 40/40 |

OTHER PUBLICATIONS

International Search Report and Written Opinion for related PCT/EP2022/063713 mailed Sep. 14, 2022.
Li et al. "Cloud Puck for Snesor Self-configuration", Sensors & Transducers, vol. 172, Issue 6, Jun. 2014, pp. 45-50.
"Lightweight Machine to Machine Technical Specificaiton: Core", Open Mobile Alliance, Nov. 10, 2020, pp. 118-122.
Hagen "IPv6 Essentials," 2nd Edition, 1st Print, O'Reilly Japan, 2008, pp. 281-300.

* cited by examiner

AUTOMATIC REGISTRATION OF AT LEAST ONE DEVICE IN A LABORATORY SYSTEM

TECHNICAL FIELD

The present invention refers to a computer-implemented method for automatic registration of at least one device in a laboratory system, a communication network for a laboratory system, a computer program comprising instructions and computer-readable storage medium. The method and device specifically may be used in the field of medical or chemical laboratories. Other fields of application of the present invention, however, are feasible.

BACKGROUND ART

Currently, for the installation or registration of any new device or module in a laboratory, a sequence of manual repetitive configuration tasks have to be followed, with high risk of introducing errors during installation. For example, there may be many different modules to be installed separately, which would be very tedious to do manually. This may have an impact on serviceability, performance data and the like.

In other technical fields there are some examples of "plug-n-play" or self-discovery and self-configuration, including medical devices.

U.S. Pat. No. 8,549,065 B2 describes a method and a corresponding device for communicating between clients and servers of a client/server system using the standard protocol OPC UA, and for the interaction of an OPC UA client with an OPC UA server, OPC UA service calls are used. In order to integrate a transaction context in OPC UA service calls, all OPC UA servers of the system are complemented by a transaction management component, and in order to carry out transactions, appropriately configured OPC UA clients communicate with respective OPC UA servers using transactions.

US 2005/0149283A1 describes a process for calibration of a medical-technical device which is in operation as a result of mounting a new component on the medical-technical device. A medical-technical device is described which is made such that it automatically identifies the new component when a new component is mounted on the medical-technical device and displays the necessary steps for calibration of the medical-technical device based on the identification. The medical-technical device however can also be made such that it automatically identifies the newly attached component after its identification.

U.S. Pat. No. 7,680,605 B2 describes a system and methods for integrating laboratory instrumentation and applications to provide a unified control and coordination architecture under a common interface. The system provides mechanisms for detection of various hardware and software components wherein the individual functionalities and input/output data types for each component are automatically recognized and incorporated into a centralized control system that provides live monitoring of the operational status of available components.

U.S. Pat. No. 8,225,015 B2 describes systems, apparatus, and methods for adaptive, dynamic medical device connectivity. In an example, a medical device interface system includes a device interface connecting a medical device to a client system and enabling exchange of data between the medical device and the client system, the device interface includes a plug and play detector detecting a connection of the medical device to the device interface and a serial agent gathering information from the medical device via a connection between the medical device and the device interface and selecting an appropriate device driver to operate and interact with the medical device connected to the device interface regardless of a presence or absence of an existing plug and play capability of the medical device.

In "Cloud PUCK for Sensor Selfconfiguration" Sensors & Transducers, Vol. 172, Issue 6, June 2014, pp. 45-50 a MBARI PUCK is described for minimizing human intervention during instrument configuration. An instrument puck is preloaded to the instrument before the instrument is plugged physically into the sensor network. It stores all the configuration information of the instrument, including its metadata and software. As soon as the instrument is plugged in, the system can retrieve its configuration information through the puck interface and configure it automatically. The instrument puck hardware consists of a nonvolatile flash memory device, a microcontroller, a serial transceiver, an isolated power supply and two RS-232 serial ports.

U.S. Pat. No. 7,535,854 B2 describes a method of device management relating to communication technology, wherein the method comprises the following steps of: the device initiatively sending a IP packet for management registration request to a management system according to address information of the management system, the request packet at least comprising the unique device identifier and IP address of the device; after the management system receiving registration request of the device, judging whether this device is legal or not according the unique device identifier, if it is, accepting the registration, otherwise rejecting. Dynamic configuration of the device can be performed through standard DHCP (Dynamic Host Configuration Protocol) procedure; encryption manner can be adopted for the IP packet for management registration request and its response packet; the device sends the management registration packets to management system at every internal.

EP 1 926 429 B1 describes a method, a system and a device for automated configuration of a high power X-ray source apparatus, which has multiple modules. A first module of the high power X-ray source apparatus has an identification unit storing at least one parameter of the first module and transmitting the parameters to a configuration control unit. At least one operating parameter of a second module is determined by the configuration control unit based on characteristics of the transmitted parameter of the first module. The high power X-ray source apparatus is configured by setting the operating parameter of the second module to the determined value.

US 2012/0110200 A1 describes a multiprotocol adapter system and a data conversion method in the multiprotocol adapter system. The multiprotocol adapter system may include a connection recognizing unit to recognize a connection with a plurality of different kinds of devices; a session managing unit to manage a connection session by sensing an input signal of the plurality of different kinds of devices connected by an input, to manage the connection with the devices; a plug and play unit to control the plurality of different kinds of devices by a unit of service provided by the plurality of different kinds of devices; a data converting unit to convert data received; a user information managing unit to manage user identity information received via radio frequency identification; and a data transmitting unit to combine the converted data and the user identity information and transmit the combined data to a terminal.

Despite this achievements in other technical fields, there is, until now, no solution that would allow automatize installation or registration of devices in a laboratory environment. A laboratory environment is a strictly regulated environment, in particular of medical devices, impacting patient testing results. For example, a laboratory needs to document the working processes for accreditation. However, changes may not be properly reported or documented, or multiple system components (e.g. >10) may need to work together in order to deliver on their common purpose. This may result in that errors might be introduced via manual configuration.

EP 3 451 253 A1 describes a method for operating a laboratory system comprising laboratory instruments and a laboratory information system. The method comprising: grouping laboratory instruments into instrument cluster(s) and providing a cluster manager thereto; the plurality of laboratory instruments publishing their instrument resource descriptions; each cluster manager maintaining an inventory of cluster resources and publishing a list of processing capabilities of the instrument cluster; the laboratory information system assigning processing of test order(s) to instrument clusters; each cluster manager assigning resources of the laboratory instruments corresponding to test order from the laboratory information system in view of the of cluster resources and each laboratory instrument carrying out the processing step(s) on the biological sample as instructed by the cluster manager.

Problem to be Solved

It is therefore desirable to provide a computer-implemented method and a communication network for a laboratory system which at least partially address the above-mentioned technical challenges. Specifically, it is desirable to provide a method and a system which allow reducing errors during installation of devices to be registered in a laboratory system and reducing manual task during installation of devices to be registered in a laboratory system.

SUMMARY

This problem is addressed by a computer-implemented method and a communication network for a laboratory system with the features of the independent claims. Advantageous embodiments which might be realized in an isolated fashion or in any arbitrary combinations are listed in the dependent claims as well as throughout the specification.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present invention, a computer-implemented method of automatic registration of at least one device in a laboratory system is disclosed.

The term "computer-implemented method" as used herein is a broad term and is to be given its ordinary and customary meaning to a person of ordinary skill in the art and is not to be limited to a special or customized meaning. The term specifically may refer, without limitation, to a method involving at least one computer and/or at least one computer network. The computer and/or computer network may comprise at least one processor which is configured for performing at least one of the method steps of the method according to the present invention. Specifically, each of the method steps is performed by the computer and/or computer network. The method may be performed completely automatically, specifically without manual action and/or user interaction.

The term "automatic" as used herein is a broad term and is to be given its ordinary and customary meaning to a person of ordinary skill in the art and is not to be limited to a special or customized meaning. The term specifically may refer, without limitation, to a process which is performed completely by means of at least one computer and/or computer network and/or machine, in particular without manual action and/or interaction with a user.

The term "laboratory system" as used herein is a broad term and is to be given its ordinary and customary meaning to a person of ordinary skill in the art and is not to be limited to a special or customized meaning. The term specifically may refer, without limitation, to at least one environment comprising a plurality of laboratory instruments such as at least one analyzer and/or at least one instrument configured for analyzing at least one sample, in particular at least one biological sample. The laboratory system may be a location configured for work in the field of the natural sciences and/or engineering in the sense that it offers the opportunity to conduct corresponding measurements and controls. The term "system", as used herein, may generally refer to an arbitrary set of interacting components being configured for interacting in order to perform at least one common task. Specifically, the components of the laboratory system may interact with each other in order to perform at least one laboratory task. The at least two components may be handled independently or may be coupled or connectable. The laboratory system specifically may be or may comprise an automated laboratory system configured for automatically or semi-automatically processing a plurality of samples, specifically a large number of samples. As an example, the laboratory system may be or may comprise an automated laboratory analyzer. The laboratory system specifically may be used in the field of medical laboratories, such as in clinical laboratories or in forensic laboratories, and/or in the field of chemical laboratories, such as in analytic laboratories. For exemplary embodiments of laboratory systems which may also be used in the context of the present invention, with the modifications as discussed herein, reference may be made e.g. to WO 2015/011274 A2, EP 3056320 A1 or EP 3412603 A1. Other laboratory systems, however, may also be used.

The laboratory system comprises a plurality of laboratory devices. The term "laboratory device" as used herein is a broad term and is to be given its ordinary and customary meaning to a person of ordinary skill in the art and is not to be limited to a special or customized meaning. The term specifically may e.g. refer, without limitation, to any apparatus or apparatus component or apparatus section or module being part of the laboratory system. At least some of the laboratory devices may be operable to execute one or more processing steps or workflow steps on one or more samples. The processing steps may comprise physically executing processing steps such as centrifugation, aliquotation, sample analysis and the like. Specifically, the laboratory devices may be or may comprise at least one laboratory instrument. The term "laboratory instrument" may cover e.g. pre-analytical instruments, post-analytical instruments, and/or analytical instruments.

The term "sample" as used herein is a broad term and is to be given its ordinary and customary meaning to a person of ordinary skill in the art and is not to be limited to a special or customized meaning. The term specifically may refer, without limitation, to an aliquot of a substance such as a chemical or biological compound. Specifically, the sample may be or may comprise at least one biological specimen, such as one or more of: blood; blood serum; blood plasma; urine; saliva. Additionally or alternatively, the sample may be or may comprise a chemical substance or compound and/or a reagent.

Analyzing a sample may comprise the laboratory devices performing at least one workflow. The term "workflow", also denoted as "processing workflow", as used herein is a broad term and is to be given its ordinary and customary meaning to a person of ordinary skill in the art and is not to be limited to a special or customized meaning. The term specifically may refer, without limitation, to a collection of workflow steps or processing steps. For example, the workflow may defines a sequence in which the workflow steps or processing steps are carried out by the laboratory devices. The workflow, in particular laboratory devices participating in the workflow and/or order of laboratory devices in the workflow and/or optimal route through the laboratory system and/or actions performed by the respective laboratory devices, may be defined by at least one laboratory configuration and layout manager such as by a management software, also denoted as solution managing software, of the laboratory system.

The registered laboratory devices may be controllable at least partially via at least one communication network. The term "communication network" as used herein is a broad term and is to be given its ordinary and customary meaning to a person of ordinary skill in the art and is not to be limited to a special or customized meaning. The term specifically may refer, without limitation, to a group of interconnected nodes. Thus, the communication network may comprise a plurality of nodes, also denoted as network nodes. Here, nodes should be understood to mean assemblies that can communicate with one another and can interchange data and/or commands. The communication network preferably comprises more than two of such nodes, for example three, four, or more of such network nodes. The laboratory devices may be nodes of the communication network. A laboratory communication and managing unit may be a further node of the communication network. The communication network may comprise further nodes such as a remote infrastructure as will be described in more detail below. The communication network may comprise a plurality of communication interfaces for communication between the nodes of the communication network. The controlling may comprise providing one or more parameters to the laboratory devices such as for communication and/or configuration. The term "at least partially" as used herein is a broad term and is to be given its ordinary and customary meaning to a person of ordinary skill in the art and is not to be limited to a special or customized meaning. The term specifically may refer, without limitation, to embodiments in which the laboratory devices are completely controllable via the communication network and embodiments wherein manual tasks are performed for controlling at least some functions of the laboratory device such as in case of failures.

The communication network may be configured for providing at least one specific configuration parameter to the registered laboratory devices, which enables the respective laboratory device to make optimal use of its feature set in the integrated lab environment such as speed, activities, torque and the like. The specific configuration parameters may be adjusted to or may depend upon conditions of the laboratory system such as a number of laboratory devices and/or a number of laboratory devices designed for performing a specific task, and in this case, may be also denoted as solution specific configuration parameters. In order to allow providing solution specific configuration parameters all laboratory devices of the laboratory system need to be registered, such as in a database comprising information of one or more of a device type, an ownership, device version information, manufacturing information, a device code, communication protocol version, e.g. capabilities of interaction.

The term "database" as used herein is a broad term and is to be given its ordinary and customary meaning to a person of ordinary skill in the art and is not to be limited to a special or customized meaning. The term specifically may refer, without limitation, to an organized collection of data, generally stored and accessed electronically from a computer or computer system. The database may comprise or may be comprised by a data storage device. The database may comprise at least one data base management system, comprising a software running on a computer or computer system, the software allowing for interaction with one or more of a user, an application or the database itself, such as in order to capture and analyze the data contained in the database. The database management system may further encompass facilities to administer the database. The database, containing the data, may, thus, be comprised by a data base system which, besides the data, comprises one or more associated applications. The database may be a remote database and/or may be part of the laboratory system.

The term "registration" as used herein is a broad term and is to be given its ordinary and customary meaning to a person of ordinary skill in the art and is not to be limited to a special or customized meaning. The term specifically may refer, without limitation, to a process of including a device into the laboratory system. The registration may comprise configuration of the device to be registered and performance improvement of the laboratory system. The registration may comprise one or more of creating a new database entry, providing solution specific configuration to the device to be registered, confirming the solution specific configuration by the device. As will be outlined in more detail below, the registration further comprises a laboratory configuration in which the solution specific configuration comprised by the registered devices is updated due to presence of the new device in the laboratory system. The device to be registered may be also denoted as "new device" herein for distinguishing it from the devices already present in the laboratory system.

The device to be registered may be a device selected from the group consisting of: at least one decapper; at least one transport system; at least one analytical instrument; at least one recapper; at least one alliquoter; at least one centrifuge, at least one tube sorter; at least one storage unit, at least one bulk tube loader; at least one tube testing station; at least one pre-analytic system. The term "device to be registered" may also refer to device components e.g. a standard power supply, which may be configured according to the use and need within the system.

The method comprises the following steps which specifically may be performed in the given order. It shall be noted, however, that a different order is also possible. Further, it is also possible to perform one or more of the method steps once or repeatedly. Further, it is possible to perform two or more of the method steps simultaneously or in a timely overlapping fashion. The method may comprise further method steps which are not listed.

i) at least one initializing step, wherein the initializing step comprises transmitting from the device to be registered device specific information to at least one laboratory communication and managing unit via at least one first communication interface;

ii) at least one device configuration step, wherein the device configuration step comprises the laboratory communication and managing unit requesting, based on the device specific information, a solution specific configuration from at least one remote infrastructure via at least one second communication interface, wherein the device configuration step comprises receiving the solution specific configuration from the remote infrastructure by the laboratory communication and managing unit via the second communication interface and transmitting the solution specific configuration from the laboratory communication and managing unit to the device to be registered via the first communication interface, wherein the solution specific configuration is based on the device specific information and configuration information about the laboratory system;

iii) at least one laboratory configuration step, wherein the laboratory configuration step comprises transmitting at least one prompt from the laboratory communication and managing unit comprising updated solution specific configuration to the laboratory devices of the laboratory system via their respective communication interface, wherein the updated solution specific configuration comprises information about the device to be registered and changes due to addition of said device to the laboratory system, wherein the laboratory configuration step further comprises providing the updated solution specific configuration to the remote infrastructure.

The present invention may allow automatic registration of the device to be registered. A laboratory configuration adjustment is possible and automatic remote interventions, in particular self-maintenance of a remote infrastructure's database. The present invention may allow that laboratory instruments can self-register such that reducing of manual registration is possible. Moreover, the laboratory instruments may be able to communicate to the remote infrastructure in the laboratory environment.

The term "initializing" as used herein is a broad term and is to be given its ordinary and customary meaning to a person of ordinary skill in the art and is not to be limited to a special or customized meaning. The term specifically may refer, without limitation, to a process of indication that a new device is available to the laboratory system. The initializing may comprise a so-called "handshaking" of the new device with the communication network.

The term "communication interface" as used herein is a broad term and is to be given its ordinary and customary meaning to a person of ordinary skill in the art and is not to be limited to a special or customized meaning. The term specifically may refer, without limitation, to an item or element forming a boundary configured for transferring information. In particular, the communication interface may be configured for transferring information from a computational device, e.g. a computer, such as to send or output information, e.g. onto another device. Additionally or alternatively, the communication interface may be configured for transferring information onto a computational device, e.g. onto a computer, such as to receive information. The communication interface may specifically provide means for transferring or exchanging information. In particular, the communication interface may provide a data transfer connection, e.g. Bluetooth, NFC, inductive coupling or the like. As an example, the communication interface may be or may comprise at least one port comprising one or more of a network or internet port, a USB-port and a disk drive. For example, the communication interface may be at least one web interface. For example, the nodes of the communication network may be configured for communicate via the internet. The communication network may comprise a plurality of communication interfaces. The communication interfaces may be designed identical or different. The terms "first", "second" and "third" and the likes are used as names herein. Data transfer via the communication interfaces may be implemented as a proprietary protocol, in particular comprising a version monitoring and/or being backwards compatible and enhanced over time, e.g. by using at least one reference USB interface.

The term "laboratory communication and managing unit" as used herein is a broad term and is to be given its ordinary and customary meaning to a person of ordinary skill in the art and is not to be limited to a special or customized meaning. The term specifically may refer, without limitation, to an arbitrary unit configured for providing communication between the laboratory devices and/or with at least one remote device such as the remote infrastructure and/or configured for managing the laboratory system such as determining and/or defining a role distribution of laboratory devices. The laboratory communication and managing unit may be designed as middleware. The term "middleware" as used herein is a broad term and is to be given its ordinary and customary meaning to a person of ordinary skill in the art and is not to be limited to a special or customized meaning. The term specifically may refer, without limitation, to a computer software that provides a platform and an interface for the communication between different application programs above the level of the operating system of the computer.

The laboratory communication and managing unit may be configured for communicating with the laboratory devices such as for interchanging data and/or commands. The laboratory communication and managing unit may be configured for wireless communicating with the laboratory devices such as via WLAN, Bluetooth, NFC and the like. The laboratory communication and managing unit may be arranged between a laboratory device-side and back-end resource, e.g. owned by the remote infrastructure.

The laboratory communication and managing unit may comprise the laboratory configuration and layout manager. The laboratory configuration and layout manager may be embodied as solution managing software. For example, the laboratory configuration and layout manager may be realized by the COBAS INFINITY® solution of Roche.

The term "device specific information" as used herein is a broad term and is to be given its ordinary and customary meaning to a person of ordinary skill in the art and is not to be limited to a special or customized meaning. The term specifically may refer, without limitation, to information for identifying the device to be registered and/or properties of the device to be registered such as one or more of functional properties, entity properties and the like. The device specific information may relate to a device's feature set such as possible ranges for operating parameters. The device specific information may comprise one or more of version information, manufacturing information, ownership information, information about software version, a device code. The device code may be comparable to FIN=SCIN (System Component Identification Number). The device code may relate to a purpose of use. For example, the device specific information may relate to a function of the device. The device specific information may be pre-loaded on the device to be registered. For example, the device specific information may have been pre-loaded on a manufacturer site. Additionally or alternatively, the device specific information may be retrieved during at least one installation step of the device to the registered such as during initial setup of the device to be registered.

The device specific information may comprise or may be transmitted in the form of at least one message. For example, when a new instrument or module is first plugged into the communication network, it may sends out a message for handshaking with the communication network. For example, in case of a decapper as new device, the device to be registered may send a handshake saying e.g. 'I'm a device of company X and I have this device code', wherein the device code may correspond to the purpose to act as a decapper.

The initializing step may comprise the laboratory communication and managing unit determining whether a software version present on the device to be registered needs to be updated and updating the software version in case a need is determined by the laboratory communication and managing unit. The initializing step may comprise collecting, installing and confirming required software updates of the device. In addition to software the firmware of the device may be checked in view of necessary updates and may be updated if necessary. For example, in case of the decapper, it is checked which version of software and/or firmware there is available for this decapper and whether there are needs for updates.

In particular after finalizing the potential update of software and firmware of the device, the device configuration step is performed.

The term "device configuration step" as used herein is a broad term and is to be given its ordinary and customary meaning to a person of ordinary skill in the art and is not to be limited to a special or customized meaning. The term specifically may refer, without limitation, to a process of adapting and/or adjusting the device to be registered to the existing laboratory system.

The term "configuration" as used herein is a broad term and is to be given its ordinary and customary meaning to a person of ordinary skill in the art and is not to be limited to a special or customized meaning. The term specifically may refer, without limitation, to at least one parameter set of at least one laboratory device, such as of operating parameters.

The term "remote infrastructure" as used herein is a broad term and is to be given its ordinary and customary meaning to a person of ordinary skill in the art and is not to be limited to a special or customized meaning. The term specifically may refer, without limitation, to at least one remote system configured for data storage and/or data processing and/or data managing. The remote infrastructure may comprise backend resources such as databases and file servers. The remote infrastructure may be configured for further tasks such as for providing service task and the like. The remote infrastructure may comprise one or more of at least one processing unit, at least one database such as at least one library, the at least one data base management system comprising a software allowing for interaction with one or more of a user, an application or the database itself, such as in order to capture and analyze the data contained in the database. The database management system may further encompass facilities to administer the database.

The device configuration step comprises the laboratory communication and managing unit, in particular the middleware, requesting, based on the device specific information, the solution specific configuration from the remote infrastructure via the second communication interface. The communication between the laboratory communication and managing unit and the remoter infrastructure may be performed via the internet. The remote infrastructure may be configured for receiving the device specific information. The device configuration step may comprise accessing the database of the remote infrastructure. The database may comprise configuration information about the laboratory system. For example, the database may comprise information about all laboratory devices already present in the laboratory system and, in particular their actual configuration and/or possible configuration such as possible ranges of operating parameters. The database may comprise other configuration information about the laboratory system such as sample throughput, workflows, environmental conditions, communication protocols and the like. The remote infrastructure may be configured for generating the solution specific configuration considering the device specific information and the configuration information about the laboratory system. For example, the remote infrastructure may be configured for determining the solution specific configuration by solving at least one optimization problem having the device specific information and the configuration information about the laboratory system as input. For example, the device configuration step may comprise accessing the database of the remote infrastructure considering the configuration information about the laboratory system and retrieving information of a communication protocol from the database.

The term "solution specific configuration" as used herein is a broad term and is to be given its ordinary and customary meaning to a person of ordinary skill in the art and is not to be limited to a special or customized meaning. The term specifically may refer, without limitation, to a set of parameters for the device's feature set in view of the device specific information and configuration information about the laboratory system. The solution specific configuration may be provided in the form of at least one instruction and/or at least one prompt for the device to be registered. The solution specific configuration may comprise one or more of at least one device communication protocol, speed information, configuration information such as at least one device specific configuration parameter. The device specific configuration parameter may enable the device to make optimal use of its feature set in the laboratory system. For example, the solution specific configuration may comprise one or more of required speed information such as push to the limits or stay within 60% performance, a configuration of how to handle sample decapping, e.g. turn twice the sample with a specific torque, and/or to define the device communication protocol used in this laboratory type or country to match compliance. The laboratory communication and managing unit, such as the middleware, may provide and share the solution specific configuration to the device to be registered to enable best performance and operation set for this entire laboratory type.

The term "solution" as used herein is a broad term and is to be given its ordinary and customary meaning to a person of ordinary skill in the art and is not to be limited to a special or customized meaning. The term specifically may refer, without limitation, to distribution of roles to the laboratory devices for a specific laboratory environment. The term "solution" may encompass parameter settings such as for operating parameters for each of the laboratory devices and/or for laboratory devices participating in a specific workflow. The term "solution" may encompass at least one communication protocol for the specific laboratory type or country.

The laboratory communication and managing unit receives the solution specific configuration from the remote infrastructure via the second communication interface and transmits the solution specific configuration from the laboratory communication and managing unit to the device to be registered via the first communication interface. The device configuration step may further comprise confirming the solution specific configuration by the device to be registered. The term "confirming the solution specific configuration" as used herein is a broad term and is to be given its ordinary and customary meaning to a person of ordinary skill in the art and is not to be limited to a special or customized meaning. The term specifically may refer, without limitation, to a process of indicating receipt of the solution specific configuration and/or adapting and/or adjusting the device to be registered in accordance with the received solution specific configuration.

Step i) and ii) may follow different levels depending on the device specific information. For example, a first level may comprise registration of the device specific information in the laboratory communication and managing unit and the remote infrastructure. A second level may comprise collecting, installing and confirming software updates of the device. A third level may comprise the device receiving communication protocol specific information and including them for routine use. A fourth level may comprise the device receiving at least one device specific configuration parameter for enabling the device to make optimal use of its feature set in the laboratory system.

The term "laboratory configuration step" as used herein is a broad term and is to be given its ordinary and customary meaning to a person of ordinary skill in the art and is not to be limited to a special or customized meaning. The term specifically may refer, without limitation, to a process of adapting and/or adjusting the laboratory devices of the laboratory system with respect to presence of a new device.

The laboratory configuration step may comprise adapting a performance of the laboratory system and/or a performance of laboratory devices depending on the updated solution specific configuration. The present invention may propose the device, which was added to the laboratory system via steps i) and ii), and resulting capabilities within the solution triggering "reaction" of the entire solution, and, in particular adaption of an overall performance or performance of other laboratory devices. The overall performance or performance of the laboratory devices may be balanced in view of the new device. For example, in case a second decapper is installed, a required sample throughput may be automatically shared between the two existing decappers. For example, it may be possible to trigger e.g. sleep mode to enhance greening and, thus, less footprint.

The laboratory configuration step comprises transmitting the prompt from the laboratory communication and managing unit comprising updated solution specific configuration to the laboratory devices of the laboratory system via their respective communication interface. The term "prompt to the laboratory devices" as used herein is a broad term and is to be given its ordinary and customary meaning to a person of ordinary skill in the art and is not to be limited to a special or customized meaning. The term specifically may refer, without limitation, to a request to the laboratory devices to make an input. Said input may result in adaption and/or adjusting a setting of the respective laboratory device. The laboratory configuration step further may comprise confirming the updated solution specific configuration by the laboratory devices. After confirmation the laboratory devices may run and/or work with and/or based on the updated solution specific configuration.

The term "updated solution specific configuration" as used herein is a broad term and is to be given its ordinary and customary meaning to a person of ordinary skill in the art and is not to be limited to a special or customized meaning. The term specifically may refer, without limitation, to information about changes and/or adaptions of previous solution specific configuration under consideration of the device registered via steps i) and ii). The laboratory communication and managing unit may update the previous solution specific configuration of the other laboratory devices considering the solution specific configuration received from the remote infrastructure in step ii). The laboratory communication and managing unit, in particular the middleware, may send out the updated solution specific configuration to other laboratory devices in the solution, which takes into account the newly installed device and any changes this may have on other devices or parameters at solution level. The updated solution specific configuration comprises information about the device to be registered and changes due to addition of said device to the laboratory system.

The laboratory configuration step further comprises providing the updated solution specific configuration to the remote infrastructure. This may ensure having the database of the remote infrastructure up-to-date allowing integration of further devices in subsequent registrations.

This invention, specifically, goes beyond merely ensuring communication between the devices of the laboratory. The present invention, in particular, proposes specific content to be communicated between the laboratory devices, which allows self-configuration and localization of the devices, as well as prompting a configuration update at solution level as a consequence of the new device being installed. For example, in contrast to U.S. Pat. No. 7,535,854 B2, the configuration of the new device depends on at least one parameter of the solution in the laboratory environment.

More specific items can be taken into consideration and standard naming may be applied. Ownership can be shared, e.g. in case of different owners of laboratory devices. The received information can be used and actions can be based on that. Similarly, with respect to US 2005/0149283A1, the present invention, in particular, goes beyond pure registration. It is about configuration and performance improvement based on components installed in the solution. The invention, in particular, proposes a workflow, wherein the new device is not to only being configured according to the other devices present in the laboratory, but the addition of the device has as well an impact in the configuration of the others. The process of EP 3 451 253 A1 can be significantly improved because the processing capabilities are optimized and not just added, and the sample processing information can be based on an ideal solution specific configuration taking into account the interdependencies of the added device and the solution specific configuration resulting in the updated solution specific configuration. This may allow an improved inclusion of the technical capabilities of the new device considering and/or taking into account the whole installed laboratory system.

In a further aspect of the invention, a communication network for a laboratory system is proposed. The communication network is configured for performing the method according to the present invention, such as according to any one of the embodiments disclosed with respect to the method above and/or according to any one of the embodiments disclosed in further detail below.

The laboratory system comprises a plurality of laboratory devices each having at least one communication interface, wherein the communication network comprises at least one laboratory communication and managing unit. The laboratory communication and managing unit is configured for receiving device specific information from a device to be registered transmitted from said device via at least one first communication interface. The laboratory communication and managing unit is configured for requesting, based on the device specific information, a solution specific configuration from at least one remote infrastructure via at least one second communication interface. The laboratory communication and managing unit is configured for receiving the solution specific configuration from the remote infrastructure via the second communication interface and transmitting the solution specific configuration from the laboratory communication and managing unit to the device to be registered via the first communication interface. The solution specific configuration is based on the device specific information and configuration information about the laboratory system. The laboratory communication and managing unit is configured for transmitting at least one prompt comprising updated solution specific configuration to the laboratory devices of the laboratory system via their respective communication interface. The updated solution specific configuration comprises information about the device to be registered and changes due to addition of said device to the laboratory system. The laboratory communication and managing unit is configured for providing the updated solution specific configuration to the remote infrastructure.

In a further aspect of the invention, a laboratory system comprising a plurality of laboratory devices each having at least one communication interface is proposed. The laboratory system further comprises a communication network according to the present invention. With respect to embodiments of the laboratory system reference is made to definitions and embodiments given with respect to the method according to the present invention, such as according to any one of the embodiments disclosed with respect to the method above and/or according to any one of the embodiments disclosed in further detail below.

Further disclosed and proposed herein is a computer program including computer-executable instructions for performing the method according to the present invention in one or more of the embodiments enclosed herein when the program is executed on a computer or computer network, in particular when the program is executed by the communication network according to the present invention causing the communication network to perform the method according to the present invention. Specifically, the computer program may be stored on a computer-readable data carrier and/or on a computer-readable storage medium.

As used herein, the terms "computer-readable data carrier" and "computer-readable storage medium" specifically may refer to non-transitory data storage means, such as a hardware storage medium having stored thereon computer-executable instructions. The computer-readable data carrier or storage medium specifically may be or may comprise a storage medium such as a random-access memory (RAM) and/or a read-only memory (ROM).

Thus, specifically, one, more than one or even all of method steps i) to iii) as indicated above may be performed by using a computer or a computer network, preferably by using a computer program.

Further disclosed and proposed herein is a computer program product having program code means, in order to perform the method according to the present invention in one or more of the embodiments enclosed herein when the program is executed on a computer or computer network. Specifically, the program code means may be stored on a computer-readable data carrier and/or on a computer-readable storage medium.

Further disclosed and proposed herein is a data carrier having a data structure stored thereon, which, after loading into a computer or computer network, such as into a working memory or main memory of the computer or computer network, may execute the method according to one or more of the embodiments disclosed herein.

Further disclosed and proposed herein is a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier and/or on a computer-readable storage medium. Specifically, the computer program product may be distributed over a data network.

Finally, disclosed and proposed herein is a modulated data signal which contains instructions readable by a computer system or computer network, for performing the method according to one or more of the embodiments disclosed herein.

Referring to the computer-implemented aspects of the invention, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, further disclosed herein are:

a computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer program, wherein the computer program is adapted to perform the method according to one of the embodiments described in this description while the program is being executed on a computer, a computer program comprising program means for performing the method according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing the method according to one of the embodiments described in this description, if the program code means are executed on a computer or on a computer network.

Summarizing and without excluding further possible embodiments, the following embodiments may be envisaged:

Embodiment 1. A computer-implemented method of automatic registration of at least one device in a laboratory system, wherein the laboratory system comprises a plurality of laboratory devices, the method comprises the following steps:

i) at least one initializing step, wherein the initializing step comprises transmitting from the device to be registered device specific information to at least one laboratory communication and managing unit via at least one first communication interface;

ii) at least one device configuration step, wherein the device configuration step comprises the laboratory communication and managing unit requesting, based on the device specific information, a solution specific configuration from at least one remote infrastructure via at least one second communication interface, wherein the device configuration step comprises receiving the solution specific configuration from the remote infrastructure by the laboratory communication and managing unit via the second communication interface and transmitting the solution specific configuration from the laboratory communication and managing unit to the device to be registered via the first communication interface, wherein the solution specific configuration is based on the device specific information and configuration information about the laboratory system;

iii) at least one laboratory configuration step, wherein the laboratory configuration step comprises transmitting at least one prompt from the laboratory communication and managing unit comprising updated solution specific configuration to the laboratory devices of the laboratory system via their respective communication interface, wherein the updated solution specific configuration comprises information about the device to be registered and changes due to addition of said device to the laboratory system, wherein the laboratory configuration step further comprises providing the updated solution specific configuration to the remote infrastructure.

Embodiment 2. The method according to the preceding embodiment, wherein the device to be registered is a device selected from the group consisting of: at least one decapper; at least one transport system; at least one analytical instrument; at least one recapper; at least one alliquoter; at least one centrifuge, at least one tube sorter; at least one storage unit, at least one bulk tube loader; at least one tube testing station; at least one pre-analytic system.

Embodiment 3 The method according to any one of the preceding embodiments, wherein the device specific information comprises one or more of version information, manufacturing information, ownership information, information about software version, a device code, communication protocol version.

Embodiment 4. The method according to any one of the preceding embodiments, wherein step i) comprises the laboratory communication and managing unit determining whether a software version present on the device needs to be updated and updating the software version in case a need is determined by the laboratory communication and managing unit.

Embodiment 5. The method according to any one of the preceding embodiments, wherein the solution specific configuration comprises one or more of at least one device communication protocol, speed information, configuration information such as at least one device specific configuration parameter.

Embodiment 6. The method according to any one of the preceding embodiments, wherein steps i) and ii) follow different levels depending on the device specific information, wherein a first level comprises registration of the device specific information in the laboratory communication and managing unit and the remote infrastructure, wherein a second level comprises collecting, installing and confirming software updates of the device, wherein a third level comprises the device receiving communication protocol specific information and including them for routine use, wherein a fourth level comprises the device receiving at least one device specific configuration parameter for enabling the device to make optimal use of its feature set in the laboratory system.

Embodiment 7. The method according to any one of the preceding embodiments, wherein the laboratory configuration step comprises adapting a performance of the laboratory system and/or a performance of laboratory devices depending on the updated solution specific configuration.

Embodiment 8. The method according to any one of the preceding embodiments, wherein the device configuration step further comprises confirming the solution specific configuration by the device to be registered.

Embodiment 9. The method according to any one of the preceding embodiments, wherein the laboratory configuration step further comprises confirming the updated solution specific configuration by the laboratory devices.

Embodiment 10. The method according to any one of the preceding embodiments, wherein the laboratory communication and managing unit is configured for communicating with the laboratory devices.

Embodiment 11. The method according to any one of the preceding embodiments, wherein the laboratory communication and managing unit is configured for wireless communicating with the laboratory devices.

Embodiment 12. The method according to any one of the preceding embodiments, wherein the laboratory communication and managing unit is designed as middleware.

Embodiment 13. A communication network for a laboratory system, wherein the communication network is configured for performing the method according to any one of the preceding embodiments, wherein the laboratory system comprises a plurality of laboratory devices each having at least one communication interface, wherein the communication network comprises at least one laboratory communication and managing unit, wherein the laboratory communication and managing unit is configured for receiving device specific information from a device to be registered transmitted from said device via at least one first communication interface, wherein the laboratory communication and managing unit is configured for requesting, based on the device specific information, a solution specific configuration from at least one remote infrastructure via at least one second communication interface, wherein the laboratory communication and managing unit is configured for receiving the solution specific configuration from the remote infrastructure via the second communication interface and transmitting the solution specific configuration from the laboratory communication and managing unit to the device to be registered via the first communication interface, wherein the solution specific configuration is based on the device specific information and configuration information about the laboratory system, wherein the laboratory communication and managing unit is configured for transmitting at least one prompt comprising updated solution specific configuration to the laboratory devices of the laboratory system via their respective communication interface, wherein the updated solution specific configuration comprises information about the device to be registered and changes due to addition of said device to the laboratory system, wherein the laboratory communication and managing unit is configured for providing the updated solution specific configuration to the remote infrastructure.

Embodiment 14. A laboratory system comprising a plurality of laboratory devices each having at least one communication interface, wherein the laboratory system further comprises a communication network according to the preceding embodiment.

Embodiment 15. A computer program comprising instructions which, when the program is executed by the communication network according to embodiment 13, cause the communication network to perform the method according to any one of the preceding embodiments referring to a method.

Embodiment 16. A computer-readable storage medium comprising instructions which, when the program is executed by the communication network according to embodiment 13, cause the communication network to perform the method according to any one of the preceding embodiments referring to a method.

SHORT DESCRIPTION OF THE FIGURES

Further optional features and embodiments will be disclosed in more detail in the subsequent description of embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

Figure 2:
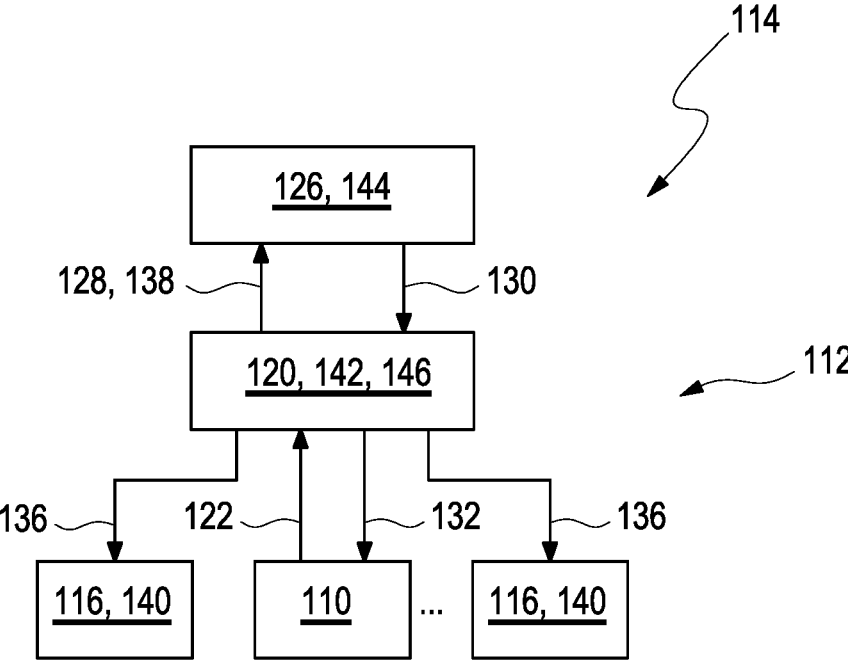

In the Figures:

FIG. 1 shows a flowchart of an exemplary embodiment of a method according to the present invention; and FIG. 2 shows an exemplary embodiment of a communication network according to the present invention.

DETAILED DESCRIPTION OF THE EMBODIMENTS

FIG. 1 shows a flowchart of an exemplary embodiment of a computer-implemented method of automatic registration of at least one device 110 in a laboratory system 112 according to the present invention. FIG. 2 shows an exemplary embodiment of a communication network 114 of the laboratory system 112 according to the present invention. The laboratory system 112 comprises a plurality of laboratory devices 116.

The method comprises the following steps which specifically may be performed in the given order. It shall be noted, however, that a different order is also possible. Further, it is also possible to perform one or more of the method steps once or repeatedly. Further, it is possible to perform two or more of the method steps simultaneously or in a timely overlapping fashion. The method may comprise further method steps which are not listed.

The method comprises the following steps:

i) (denoted with reference number 118) at least one initializing step, wherein the initializing step comprises transmitting from the device 110 to be registered device specific information to at least one laboratory communication and managing unit 120 via at least one first communication interface (denoted with arrow 122);

ii) (denoted with reference number 124) at least one device configuration step, wherein the device configuration step comprises the laboratory communication and managing unit 120 requesting, based on the device specific information, a solution specific configuration from at least one remote infrastructure 126 via at least one second communication interface (denoted with arrow 128), wherein the device configuration step comprises receiving the solution specific configuration from the remote infrastructure 126 by the laboratory communication and managing unit 120 via the second communication interface (denoted with arrow 130) and transmitting the solution specific configuration from the laboratory communication and managing unit 120 to the device 110 to be registered via the first communication interface (denoted with arrow 132), wherein the solution specific configuration is based on the device specific information and configuration information about the laboratory system 112;

iii) (denoted with reference number 134) at least one laboratory configuration step, wherein the laboratory configuration step comprises transmitting at least one prompt from the laboratory communication and managing unit 120 comprising updated solution specific configuration to the laboratory devices 116 of the laboratory system 112 via their respective communication interface (denoted with arrow 136), wherein the updated solution specific configuration comprises information about the device 110 to be registered and changes due to addition of said device 110 to the laboratory system 112, wherein the laboratory configuration step further comprises providing the updated solution specific configuration to the remote infrastructure 126 (denoted with arrow 138).

The laboratory device 116 may be an apparatus or apparatus component or apparatus section or module being part of the laboratory system 112. At least some of the laboratory devices 116 may be operable to execute one or more processing steps or workflow steps on one or more samples. The processing steps may comprise physically executing processing steps such as centrifugation, aliquotation, sample analysis and the like. The laboratory system 112 may comprise a plurality of laboratory instruments 140 such as at least one analyzer and/or at least one instrument configured for analyzing at least one sample, in particular at least one biological sample. The laboratory instruments 140 may be pre-analytical instruments, post-analytical instruments, and/ or analytical instruments. The laboratory system 112 may be a location configured for work in the field of the natural sciences and/or engineering in the sense that it offers the opportunity to conduct corresponding measurements and controls. The laboratory system 112 specifically may be or may comprise an automated laboratory system configured for automatically or semi-automatically processing a plurality of samples, specifically a large number of samples. As an example, the laboratory system 112 may be or may comprise an automated laboratory analyzer. The laboratory system 112 specifically may be used in the field of medical laboratories, such as in clinical laboratories or in forensic laboratories, and/or in the field of chemical laboratories, such as in analytic laboratories.

The sample may be an aliquot of a substance such as a chemical or biological compound. Specifically, the sample may be or may comprise at least one biological specimen, such as one or more of: blood; blood serum; blood plasma; urine; saliva. Additionally or alternatively, the sample may be or may comprise a chemical substance or compound and/or a reagent. Analyzing a sample may comprise the laboratory devices 116 performing at least one workflow. The workflow, in particular laboratory devices 116 participating in the workflow and/or order of laboratory devices 116 in the workflow and/or optimal route through the laboratory system 112 and/or actions performed by the respective laboratory devices 116, may be defined by at least one laboratory configuration and layout manager 142 such as by a management software, also denoted as solution managing software, of the laboratory system.

The registered laboratory devices 116 may be controllable at least partially via the at least one communication network 114. The communication network 116 may comprise a plurality of nodes. The communication network 116 preferably comprises more than two of such nodes, for example three, four, or more of such network nodes. The laboratory devices 116 may be nodes of the communication network. The laboratory communication and managing unit 120 may be a further node of the communication network 116. The communication network may comprise further nodes such as the remote infrastructure 126. The communication network 116 may comprise a plurality of communication interfaces for communication between the nodes of the communication network 116. The controlling may comprise providing one or more parameters to the laboratory devices 116 such as for communication and/or configuration.

The communication network 116 may be configured for providing at least one specific configuration parameter to the registered laboratory devices 116, which enables the respective laboratory device 116 to make optimal use of its feature set in the integrated lab environment such as speed, activities, torque and the like. The specific configuration parameters may be adjusted to or may depend upon conditions of the laboratory system 112 such as a number of laboratory devices 116 and/or a number of laboratory devices 116 designed for performing a specific task, and in this case, may be also denoted as solution specific configuration parameters. In order to allow providing solution specific configuration parameters all laboratory devices 116 of the laboratory system need to be registered, such as in a database 144 comprising information of one or more of a device type, an ownership, device version information, manufacturing information, a device code, communication protocol version, e.g. capabilities of interaction.

The database 144 may be or may comprise an organized collection of data, generally stored and accessed electronically from a computer or computer system. The database 144 may comprise or may be comprised by a data storage device. The database 144 may comprise at least one data base management system, comprising a software running on a computer or computer system, the software allowing for interaction with one or more of a user, an application or the database itself, such as in order to capture and analyze the data contained in the database. The database management system may further encompass facilities to administer the database. The database 144, containing the data, may, thus, be comprised by a data base system which, besides the data, comprises one or more associated applications. The database 144 may be a remote database (as shown in FIG. 2) and/or may be part of the laboratory system 112.

The registration of the device 110 may be a process of including the device 110 into the laboratory system 112. The registration may comprise configuration of the device 110 to be registered and performance improvement of the laboratory system 112. The registration may comprise one or more of creating a new database entry, providing solution specific configuration to the device 110 to be registered, confirming the solution specific configuration by the device 110. The registration further comprises a laboratory configuration in which the solution specific configuration comprised by the registered devices 116 is updated due to presence of the new device 110 in the laboratory system 112.

The device 110 to be registered may be a device selected from the group consisting of: at least one decapper; at least one transport system; at least one analytical instrument; at least one recapper; at least one alliquoter; at least one centrifuge, at least one tube sorter; at least one storage unit, at least one bulk tube loader; at least one tube testing station; at least one pre-analytic system.

The initializing in step i) may comprise a process of indication that the new device 110 is available to the laboratory system 112. The initializing may comprise a so-called "handshaking" of the new device 110 with the communication network 114.

The laboratory communication and managing unit 120 may be configured for providing communication between the laboratory devices 116 and/or with the at least one remote infrastructure 126. The laboratory communication and managing unit 120 may be configured for managing the laboratory system 112 such as determining and/or defining a role distribution of laboratory devices 116. The laboratory communication and managing unit 120 may be designed as middleware 146. The laboratory communication and managing unit 120 may be configured for communicating with the laboratory devices 116 such as for interchanging data and/or commands. The laboratory communication and managing unit 120 may be configured for wireless communicating with the laboratory devices 116 such as via WLAN, Bluetooth, NFC and the like. The laboratory communication and managing unit 120 may be arranged between a laboratory device-side and back-end resource, e.g. owned by the remote infrastructure 126. The laboratory communication and managing unit 120 may comprise the laboratory configuration and layout manager 142. The laboratory configuration and layout manager 142 may be embodied as solution managing software. For example, the laboratory configuration and layout manager 142 may be realized by the COBAS INFINITY® solution of Roche.

The device specific information may be information for identifying the device 110 to be registered and/or properties of the device 110 to be registered such as one or more of functional properties, entity properties and the like. The device specific information may relate to a device's 110 feature set such as possible ranges for operating parameters. The device specific information may comprise one or more of version information, manufacturing information, ownership information, information about software version, a device code, communication protocol version, e.g. capabilities of interaction. The device code may relate to a purpose of use. For example, the device specific information may relate to a function of the device 110. The device specific information may be pre-loaded on the device 110 to be registered. For example, the device specific information may have been pre-loaded on a manufacturer site. Additionally or alternatively, the device specific information may be retrieved during at least one installation step of the device 110 to the registered such as during initial setup of the device 110 to be registered.

The device specific information may comprise or may be transmitted in the form of at least one message. For example, when a new instrument or module is first plugged into the communication network, it may sends out a message for handshaking with the communication network 114. For example, in case of a decapper as new device 110, the device 110 to be registered may send a handshake saying e.g. 'I'm a device of company X and I have this device code', wherein the device code may correspond to the purpose to act as a decapper.

The initializing step 118 may comprise the laboratory communication and managing unit 120 determining whether a software version present on the device 110 to be registered needs to be updated and updating the software version in case a need is determined by the laboratory communication and managing unit 120. The initializing step 118 may comprise collecting, installing and confirming required software updates of the device 110. In addition to software the firmware of the device 110 may be checked in view of necessary updates and may be updated if necessary. For example, in case of the decapper, it is checked which version of software and/or firmware there is available for this decapper and whether there are needs for updates.

In particular after finalizing the potential update of software and firmware of the device 110, the device configuration step 124 is performed.

The device configuration step 124 may comprise a process of adapting and/or adjusting the device 110 to be registered to the existing laboratory system 112.

The remote infrastructure 126 may be or may comprise least one remote system configured for data storage and/or data processing and/or data managing. The remote infrastructure 126 may comprise backend resources such as databases and file servers. The remote infrastructure 126 may be configured for further tasks such as for providing service task and the like. The remote infrastructure 126 may comprise one or more of at least one processing unit, at least one database such as at least one library, the at least one data base management system comprising a software allowing for interaction with one or more of a user, an application or the database itself, such as in order to capture and analyze the data contained in the database. The database management system may further encompass facilities to administer the database.

The device configuration step 124 comprises the laboratory communication and managing unit 120, in particular the middleware 146, requesting, based on the device specific information, the solution specific configuration from the remote infrastructure 126 via the second communication interface (denoted with arrow 128). The communication between the laboratory communication and managing unit 120 and the remoter infrastructure 126 may be performed via the internet. The remote infrastructure 126 may be configured for receiving the device specific information. The device configuration step 124 may comprise accessing the database 144 of the remote infrastructure 126. The database 126 may comprise configuration information about the laboratory system 112. For example, the database 144 may comprise information about all laboratory devices 116 already present in the laboratory system 112 and, in particular their actual configuration and/or possible configuration such as possible ranges of operating parameters. The database 144 may comprise other configuration information about the laboratory system 112 such as sample throughput, workflows, environmental conditions, communication protocols and the like. The remote infrastructure 126 may be configured for generating the solution specific configuration considering the device specific information and the configuration information about the laboratory system 112. For example, the remote infrastructure 126 may be configured for determining the solution specific configuration by solving at least one optimization problem having the device specific information and the configuration information about the laboratory system 112 as input. For example, the device configuration step 124 may comprise accessing the database 144 of the remote infrastructure 126 considering the configuration information about the laboratory system 112 and retrieving information of a communication protocol from the database 144.

The solution specific configuration may be or may comprise a set of parameters for the device's 110 feature set in view of the device specific information and configuration information about the laboratory system 112. The solution specific configuration may be provided in the form of at least one instruction and/or at least one prompt for the device 110 to be registered. The solution specific configuration may comprise one or more of at least one device communication protocol, speed information, configuration information such as at least one device specific configuration parameter. The device specific configuration parameter may enable the device 110 to make optimal use of its feature set in the laboratory system. For example, the solution specific configuration may comprise one or more of required speed information such as push to the limits or stay within 60% performance, a configuration of how to handle sample decapping, e.g. turn twice the sample with a specific torque, and/or to define the device communication protocol used in this laboratory type or country to match compliance. The laboratory communication and managing unit 120, such as the middleware 146, may provide and share the solution specific configuration to the device 110 to be registered to enable best performance and operation set for this entire laboratory type (denoted with arrow 132).

The device configuration step 124 may further comprise confirming the solution specific configuration by the device to be registered. The confirming the solution specific configuration may comprise indicating receipt of the solution specific configuration and/or adapting and/or adjusting the device 110 to be registered in accordance with the received solution specific configuration.

Step i) 118 and ii) 124 may follow different levels depending on the device specific information. For example, a first level may comprise registration of the device specific information in the laboratory communication and managing unit 120 and the remote infrastructure 126. A second level may comprise collecting, installing and confirming software updates of the device. A third level may comprise the device 110 receiving communication protocol specific information and including them for routine use. A fourth level may comprise the device 110 receiving at least one device specific configuration parameter for enabling the device 110 to make optimal use of its feature set in the laboratory system 112.

The laboratory configuration step 134 may comprise adapting and/or adjusting the laboratory devices 116 of the laboratory system 112 with respect to presence of a new device 110. The laboratory configuration step 134 may comprise adapting a performance of the laboratory system 112 and/or a performance of laboratory devices 116 depending on the updated solution specific configuration. The present invention may propose the device 110, which was added to the laboratory system 112 via steps i) 118 and ii) 124, and resulting capabilities within the solution triggering "reaction" of the entire solution, and, in particular adaption of an overall performance or performance of other laboratory devices 116. The overall performance or performance of the laboratory devices 116 may be balanced in view of the new device 110. For example, in case a second decapper is installed, a required sample throughput may be automatically shared between the two existing decappers. For example, it may be possible to trigger e.g. sleep mode to enhance greening and, thus, less footprint.

The laboratory configuration step 134 comprises transmitting the prompt from the laboratory communication and managing unit 120 comprising updated solution specific configuration to the laboratory devices 116 of the laboratory system 112 via their respective communication interface (denoted with arrow 136). The prompt to the laboratory devices 116 may be or may comprise a request to the laboratory devices 116 to make an input. Said input may result in adaption and/or adjusting a setting of the respective laboratory device 116. The laboratory configuration step 134 further may comprise confirming the updated solution specific configuration by the laboratory devices 116. After confirmation the laboratory devices 116 may run and/or work with and/or based on the updated solution specific configuration.

The updated solution specific configuration may be or may comprise information about changes and/or adaptions of previous solution specific configuration under consideration of the device registered via steps i) 118 and ii) 124. The laboratory communication and managing unit 120 may update the previous solution specific configuration of the other laboratory devices 116 considering the solution specific configuration received from the remote infrastructure 126 in step ii) 124. The laboratory communication and managing unit 120, in particular the middleware 146, may send out the updated solution specific configuration to other laboratory devices 116 in the solution, which takes into account the newly installed device 110 and any changes this may have on other devices 116 or parameters at solution level. The updated solution specific configuration comprises information about the device 110 to be registered and changes due to addition of said device 110 to the laboratory system 112.

The laboratory configuration step 134 further comprises providing the updated solution specific configuration to the remote infrastructure 126 (denoted with arrow 138). This may ensure having the database 144 of the remote infrastructure 126 up-to-date allowing integration of further devices 110 in subsequent registrations.

As shown in FIG. 2, the communication network 114 comprises the laboratory communication and managing unit 120 which is configured for receiving device specific information from the device 110 to be registered transmitted from said device 110 via at least one first communication interface. The laboratory communication and managing unit 120 is configured for requesting, based on the device specific information, a solution specific configuration from the remote infrastructure 126 via at least one second communication interface. The laboratory communication and managing unit 120 is configured for receiving the solution specific configuration from the remote infrastructure 126 via the second communication interface and transmitting the solution specific configuration from the laboratory communication and managing unit 120 to the device 110 to be registered via the first communication interface. The solution specific configuration is based on the device specific information and configuration information about the laboratory system 112. The laboratory communication and managing unit 120 is configured for transmitting at least one prompt comprising updated solution specific configuration to the laboratory devices 116 of the laboratory system 112 via their respective communication interface. The updated solution specific configuration comprises information about the device 110 to be registered and changes due to addition of said device 110 to the laboratory system 112. The laboratory communication and managing unit 120 is configured for providing the updated solution specific configuration to the remote infrastructure 126.

LIST OF REFERENCE NUMBERS

110 device
112 laboratory system
114 communication network
116 laboratory device
118 initializing step
120 laboratory communication and managing unit
122 transmitting device specific information
124 transmitting from the device 110 to be registered device specific information
126 remote infrastructure
128 requesting solution specific configuration
130 receiving the solution specific configuration
132 transmitting solution specific configuration from the laboratory communication and managing unit to the device
134 laboratory configuration step
136 transmitting updated solution specific configuration to the laboratory devices
138 providing updated solution specific configuration to the remote infra-structure 140 laboratory instrument
142 laboratory configuration and layout manager
144 database
146 middleware

The invention claimed is:

1. A computer-implemented method of automatic registration of at least one device in a laboratory system, wherein the laboratory system comprises a plurality of laboratory devices realizing a solution specific configuration, the method comprises the following steps:

i) at least one initializing step, wherein the initializing step comprises transmitting from the device to be registered device specific information to at least one laboratory communication and managing unit via at least one first communication interface;

ii) at least one device configuration step, wherein the device configuration step comprises the laboratory communication and managing unit requesting, based on the device specific information, a solution specific configuration from at least one remote infrastructure via at least one second communication interface, wherein the device configuration step comprises receiving the solution specific configuration from the remote infrastructure by the laboratory communication and managing unit via the second communication interface and transmitting the solution specific configuration from the laboratory communication and managing unit to the device to be registered via the first communication interface, wherein the solution specific configuration is based on the device specific information and configuration information about the laboratory system;

iii) at least one laboratory configuration step, wherein the laboratory configuration step comprises transmitting at least one request from the laboratory communication and managing unit comprising updated solution specific configuration to the laboratory devices of the laboratory system via their respective communication interface, wherein the updated solution specific configuration comprises information about the device to be registered and changes due to addition of said device to the laboratory system, wherein the laboratory configuration step further comprises providing the updated solution specific configuration to the remote infrastructure.

2. The method according to claim 1, wherein the device to be registered is a device selected from the group consisting of: at least one decapper; at least one transport system; at least one analytical instrument; at least one recapper; at least one alliquoter; at least one centrifuge, at least one tube sorter; at least one storage unit, at least one bulk tube loader; at least one tube testing station; at least one pre-analytic system.

3. The method according to claim 1, wherein the device specific information comprises one or more of version information, manufacturing information, ownership information, information about software version, a device code, communication protocol version.

4. The method according to claim 1, wherein step i) comprises the laboratory communication and managing unit determining whether a software version present on the device needs to be updated and updating the software version in case a need is determined by the laboratory communication and managing unit.

5. The method according to claim 1, wherein the solution specific configuration comprises one or more of at least one device communication protocol, speed information, configuration information such as at least one device specific configuration parameter.

6. The method according to claim 1, wherein steps i) and ii) follow different levels depending on the device specific information, wherein a first level comprises registration of the device specific information in the laboratory communication and managing unit and the remote infrastructure, wherein a second level comprises collecting, installing and confirming software updates of the device, wherein a third level comprises the device receiving communication protocol specific information and including them for routine use, wherein a fourth level comprises the device receiving at least one device specific configuration parameter for enabling the device to make optimal use of its feature set in the laboratory system.

7. The method according to claim 1, wherein the laboratory configuration step comprises adapting a performance of the laboratory system and/or a performance of laboratory devices depending on the updated solution specific configuration.

8. The method according to claim 1, wherein the device configuration step further comprises confirming the solution specific configuration by the device to be registered.

9. The method according to claim 1, wherein the laboratory configuration step further comprises confirming the updated solution specific configuration by the laboratory devices.

10. The method according to claim 1, wherein the laboratory communication and managing unit is configured for communicating with the laboratory devices.

11. The method according to claim 1, wherein the laboratory communication and managing unit is configured for wireless communicating with the laboratory devices.

12. The method according to claim 1, wherein the laboratory communication and managing unit is designed as middleware.

13. A communication network for a laboratory system, wherein the communication network is configured for performing the method according to claim 1, wherein the laboratory system comprises a plurality of laboratory devices each having at least one communication interface, wherein the communication network comprises at least one laboratory communication and managing unit, wherein the laboratory communication and managing unit is configured for receiving device specific information from a device to be registered transmitted from said device via at least one first communication interface, wherein the laboratory communication and managing unit is configured for requesting, based on the device specific information, a solution specific configuration from at least one remote infrastructure via at least one second communication interface, wherein the laboratory communication and managing unit is configured for receiving the solution specific configuration from the remote infrastructure via the second communication interface and transmitting the solution specific configuration from the laboratory communication and managing unit to the device to be registered via the first communication interface, wherein the solution specific configuration is based on the device specific information and configuration information about the laboratory system, wherein the laboratory communication and managing unit is configured for transmitting at least one request comprising updated solution specific configuration to the laboratory devices of the laboratory system via their respective communication interface, wherein the updated solution specific configuration comprises information about the device to be registered and changes due to addition of said device to the laboratory system, wherein the laboratory communication and managing unit is configured for providing the updated solution specific configuration to the remote infrastructure.

14. A laboratory system comprising a plurality of laboratory devices each having at least one communication interface, wherein the laboratory system further comprises a communication network according to claim 13.

15. A computer program comprising instructions which, when the program is executed by the communication network according to claim 13, cause the communication network to perform the method comprising the following steps:

i) at least one initializing step, wherein the initializing step comprises transmitting from the device to be registered device specific information to at least one laboratory communication and managing unit via at least one first communication interface;

ii) at least one device configuration step, wherein the device configuration step comprises the laboratory communication and managing unit requesting, based on the device specific information, a solution specific configuration from at least one remote infrastructure via at least one second communication interface, wherein the device configuration step comprises receiving the solution specific configuration from the remote infrastructure by the laboratory communication and managing unit via the second communication interface and transmitting the solution specific configuration from the laboratory communication and managing unit to the device to be registered via the first communication interface, wherein the solution specific configuration is based on the device specific information and configuration information about the laboratory system;

iii) at least one laboratory configuration step, wherein the laboratory configuration step comprises transmitting at least one request from the laboratory communication and managing unit comprising updated solution specific configuration to the laboratory devices of the laboratory system via their respective communication interface, wherein the updated solution specific configuration comprises information about the device to be registered and changes due to addition of said device to the laboratory system, wherein the laboratory configuration step further comprises providing the updated solution specific configuration to the remote infrastructure.

16. A computer-readable storage medium comprising instructions which, when the program is executed by the communication network according to claim 13, cause the communication network to perform the method comprising the following steps:

i) at least one initializing step, wherein the initializing step comprises transmitting from the device to be registered device specific information to at least one laboratory communication and managing unit via at least one first communication interface;

ii) at least one device configuration step, wherein the device configuration step comprises the laboratory communication and managing unit requesting, based on the device specific information, a solution specific configuration from at least one remote infrastructure via at least one second communication interface, wherein the device configuration step comprises receiving the solution specific configuration from the remote infrastructure by the laboratory communication and managing unit via the second communication interface and transmitting the solution specific configuration from the laboratory communication and managing unit to the device to be registered via the first communication interface, wherein the solution specific configuration is based on the device specific information and configuration information about the laboratory system;

iii) at least one laboratory configuration step, wherein the laboratory configuration step comprises transmitting at least one request from the laboratory communication and managing unit comprising updated solution specific configuration to the laboratory devices of the laboratory system via their respective communication interface, wherein the updated solution specific configuration comprises information about the device to be registered and changes due to addition of said device to the laboratory system, wherein the laboratory configuration step further comprises providing the updated solution specific configuration to the remote infrastructure.

* * * * *